United States Patent [19]

Knifton

[11] Patent Number: 5,146,041

[45] Date of Patent: Sep. 8, 1992

[54] METHOD OF SEPARATING ISOBUTYLENE FROM A C-4 HYDROCARBON FRACTION USING MONTMORILLONITE CATALYSTS

[75] Inventor: John F. Knifton, Austin, Tex.

[73] Assignee: Texaco Chemical Company, White Plains, N.Y.

[21] Appl. No.: 753,502

[22] Filed: Sep. 3, 1991

[51] Int. Cl.$^5$ .......................... C07C 7/00; C07C 43/00
[52] U.S. Cl. ...................... 585/864; 585/833; 585/852; 585/853; 585/854; 585/930; 568/697
[58] Field of Search ............... 585/833, 852, 853, 854, 585/864, 930; 568/697

[56]  References Cited

U.S. PATENT DOCUMENTS 4,012,456  3/1977  Chaplits ........................... 585/864
4,448,643  5/1984  Lindner et al. .................. 585/864
4,570,026  2/1986  Keyworth et al. ................ 585/864

Primary Examiner—Anthony McFarlane
Assistant Examiner—Nhat Phan
Attorney, Agent, or Firm—Jack H. Park; Kenneth R. Priem; Cynthia L. Kendrick

[57]  ABSTRACT

Disclosed is a two-step method for separating isobutylene from a C-4 hydrocarbon fraction comprising:
  a) Reacting the C-4 fraction with a glycol in the presence of an acidic montmorillonite catalyst at a temperature of about 60° to 160° C. to yield the corresponding glycol mono-t-butyl ether, and subsequently
  b) reacting the intermediate glycol ether product over the same class of catalyst at a temperature of about 100° to 220° C. to regenerate the isolatable isobutylene.

10 Claims, No Drawings

METHOD OF SEPARATING ISOBUTYLENE FROM A C-4 HYDROCARBON FRACTION USING MONTMORILLONITE CATALYSTS

FIELD OF THE INVENTION

This invention relates to the separation of isobutylene from a C-4 hydrocarbon fraction. More particularly this invention relates to a two-step method of separating isobutylene from a C-4 hydrocarbon fraction using a montmorillonite clay catalyst.

BACKGROUND OF THE INVENTION

Separation of olefins from mixed hydrocarbon streams has long been a subject of research and process development efforts. This field includes such widespread applications as recovery of ethylene from steam cracker effluents or dilute refinery streams, $C_2$ and $C_3$ splitting, and recovery of butene-1 from mixed C-4 streams. One of the valuable olefins which can be separated out of a C-4 hydrocarbon stream is isobutylene. Isobutylene is valuable, among other uses, as a reactant in the preparation of high octane ethers such as methyl t-butyl ether and ethyl t-butyl ether, as well as ethylene and propylene glycol ethers.

In Chem Systems, Topical Reports, Vol. II, p. 1 (1988 program), Sept. 1989 there is discussed the recovery of butene-1 by complexation.

The use of complexing agents in solution for complexation of olefins to separate them from paraffins is addressed in Shell U.S. Pat. Nos. 3,401,112 and 3,449,240. Other patents describe olefin-paraffin separation by means of a selective complex formation. See Monsanto U.S. Pat. Nos. 3,517,080 and 3,517,081.

Research has demonstrated the removal of ethylene from dilute streams with cuprous containing complexes in aromatic solvents. See Esso Research and Engineering U.S. Pat. Nos. 3,592,865; 3,651,159 and 3,754,047. To review additional research in this area, see Gottesman, R. T. "A New Process for Separation of Ethylene from Low Grade Gas Streams," Technology Exchange, Chicago, Ill. (February 1977) and Gutierrez, A. P. et al. "ESEP-A Process for the Recovery of Ethylene" paper presented at the 175th ACS Meeting, Anaheim, Calif. (Mar. 12–17, 1978). An attractive process for ethylene recovery from a cat cracker off-gas was reviewed in Chem. Systems, PERP Third Quarterly Report, Section 3.00 (1978). Other complexing solutions and complexing agents incorporated into solid adsorbents and membranes are disclosed in U.S. Pat. Nos. 3,828,398 to Esso, 4,025,574 to Phillips, 4,545,966 to Walker and 3,979,280 to Deutsche Texaco.

In an article by Ho, N. S., Winston, Doyle, G., Savage, D. S. and Pruett, R. L. I.E.C. Res. 1988, 27, p. 334, there is described the use of a complexing solution for the separation of $C_2$–$C_5$ olefins and linear o-olefins from internal and branched olefins of the same carbon number. The complexing solution is covered in Esso U.S. Pat. No. 4,471,152.

In the Chem Systems, Topical Reports, Vol. II reference above at page 4, it is indicated that the complexing solution of U.S. Pat. No. 4,471,152 works best for separating ethylene and in the last paragraph there is reference to the "suppression of the complexation of internal and branched olefins." Therefore this technology teaches away from benefits in attempting to separate isobutylene. This technology is of special interest in the separation of α-olefins and, thus, more separation is expected of butene-1 and butene-2. In Section 1.22, Ibid, there is a description of the application of copper complexation technology to recovery of butene-1 from a steam cracker C-4 stream. At page 7, last paragraph it is stated this technology is selective for butene-1 compared to isobutylene and all other C-4 components.

At subtitle 1.31 on page 10, Ibid, it is stated "isobutylene and butadiene are seen to be virtually inseparable from butene-1" Technologies are discussed for butene-1 recovery.

J.P. 59,051,224-A (to Maruzen) discloses isobutylene separation from C-4 hydrocarbon distillate fraction by countercurrent reaction with ethylene glycol in the presence of a cation exchange catalyst.

In related copending applications, Ser. Nos. 07/396,209 and 07/410,168 incorporated herein in their entirety by reference, methods are described for the preparation of ethylene and propylene glycol ethers from isobutylene and the corresponding glycol over an acidic montmorillonite clay catalyst or an acidic heterogeneous or homogeneous catalyst.

J.P. 55,053,228 discloses a method for the preparation of ethylene glycol tertiary-butyl ether by reacting ethylene glycol with isobutylene in the presence of a strongly acidic cation exchange resin.

In J.P. 63,250,336 there is described a method for the preparation of propylene glycol tert-butyl ether by reacting propylene glycol with isobutylene in the presence of a strong acidic cation-exchange resin and tert-butanol.

Methods of using clays as catalysts for certain reactions are known in the art. In Chem Systems, Topical Reports, Vol. II, 1986 Program (May 1987), Section 3.00, there is an article which introduces the subject of pillared clays. There several processes are disclosed which can employ these pillared clay catalysts.

There is art which focuses on how various factors affect clay catalysts. In an article titled "Pillared Clays As Catalysts" in Catal. Rev.-Sci. Eng., 30(3), 457–499 (1988) there is a discussion of factors affecting the thermal stability of pillared clays and how the stability can be improved in the range from about 480° C. to about 800° C. The sam article also discusses the acidity of pillared clays and ways in which different treatments affect the Lewis or Bronsted sites to a varying extent.

In U.K. Patent Application GB 2179563 A (1987) there is disclosed the use of modified layered clays in reactions capable of catalysis by protons. These are clays where the interlamellar charge is sufficient only to permit expansion of the sheets to accommodate a single liquid layer. Claim 14 of this patent describes the various reactions which are known to be capable of catalysis by these clays. This work appears to deal broadly with a number of reactions.

Stabilized pillared interlayered clays are used in the invention of EP 0083 970 to carry out processes capable of catalysis by protons. The invention includes methods for preparing alcohols from olefins or olefin oxides and water or ethers from primary or secondary aliphatic alcohols, a polyol or an olefin oxide.

In EP Patent No. 0 0130 055 there is described the preparation of a boria-pillared layered montmorillonite clay. Here MTBE was produced from methanol and isobutene.

An interesting comparison of montmorillonite-derived catalysts with ion-exchange resins relating to MTBE production is found in an article titled "Methylt-Butyl Ether (MTBE) Production: A Comparison Of Montmorillonite Derived Catalysts With An Ion-Exchange Resin", Adams, et al. Clays and Clay Minerals, Vol. 34., No. 5,597–603, 1986.

The separation of particular components of C-4 streams such as isobutylene, butene-1, 1,3-butadiene, etc. in good yield and purity is obviously a desirable goal in the art. It would be especially helpful if it were possible to separate isobutylene using an efficient, commercially attractive process. The isobutylene isolated could be used to produce valuable solvents such as propylene glycol and ethylene glycol monobutyl ethers.

There does not appear to be any art suggesting the separation of isobutylene from a C-4 hydrocarbon fraction using montmorillonite clay catalysis.

It has been discovered that an acidic montmorillonite clay catalyst can be used to separate isobutylene from a C-4 fraction in two steps. It is an object of the present invention to separate isobutylene in good yield and regenerate glycol. Other objects will become apparent to those skilled in the art from the following description.

SUMMARY OF THE INVENTION

In accordance with the foregoing, the novel method of this invention for separation of isobutylene comprises reacting a C-4 rich hydrocarbon stream containing the isobutylene fraction with a glycol over an acidic montmorillonite clay to etherify the isobutylene fraction; and subsequently reacting the intermediate over the same class of catalyst at a higher temperature to give pure isobutylene and regenerated glycol.

DESCRIPTION OF THE PREFERRED EMBODIMENT

The separation of isobutylene in the instant invention may be carried out by reacting a C-4 hydrocarbon fraction in the presence of a catalyst comprising an acidic montomorillonite clay.

The method requires two steps which comprise:
1) Etherification of the isobutylene fraction of said C-4 stream (e.g. raffinate-1) with a glycol, such as, for example, ethylene glycol or 1,2-propylene glycol over an acidic montmorillonite clay catalyst to give the corresponding glycol mono-t-butyl ether, and
2) deetherification of the glycol t-butyl ether intermediate to give pure isobutylene plus regenerated glycol by reaction at higher temperature over the same class of acidic montmorillonite clay catalyst.

This can be represented for the intermediate synthesis of ethylene glycol t-butyl ether by the following equation:

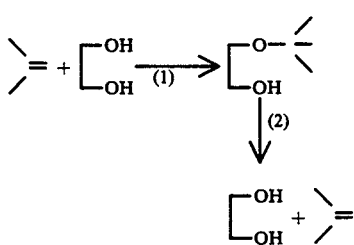

The glycols which are useful in the practice of this invention are generally diols having 2 to 20 carbon atoms per molecule. They may include vicinal glycols where the hydroxyl groups are bonded to adjacent carbon atoms, as in Eq. 1, or alternatively, the hydroxyl groupings may be separated by additional carbon atoms, as in the case of 1,3-propylene glycol and 1,6-hexane diol. Alternatively, said substrates may contain three or more hydroxyl groups per molecule, as in the case of glycerine, or they may be a polyalkylene glycol, particularly a polyethylene glycol or a polypropylene glycol containing multiple ether linkages and terminal hydroxyl groups. Said polyalkylene glycols may have molecular weights in the range of from ca. 150 to ca. 6000, and be mixtures of different polyethylene glycol or polypropylene glycol oligomers. Furthermore they may be capped or contain within the backbone, certain higher molecular weight carbon units, such as the C-4 unit, introduced during oligomerization by the addition of, for example, 1,2-butylene oxide or isobutylene oxide.

The preferred glycols for the separation of isobutylene by etherification/deetherification using acidic montmorillonite are ethylene glycol or 1,2-propylene glycol.

The molar ratio of said glycols to isobutylene in said C-4 hydrocarbon fraction in the feed mixture may vary widely, from 1:1 to 1000:1. To achieve optimum selectivities and yields of separated isobutylene it is desirable that the feed should be rich in glycol component, i.e. the molar feed ratio of glycol-to-isobutylene should be in the range 10:1 to 100:1. These conditions are illustrated in the accompanying examples.

The C-4 hydrocarbon stream used as a reactant should preferably contain a significant quantity of isobutylene. Typically, the isobutylene concentration in said C-4 hydrocarbon mix should be in the range 1–50%. Other compounds commonly found in such a stream include, for example, isobutane, butene-1, 1,3-butadiene, n-butane, trans-butene-2, and cis-butene-2. Suitable feedstocks include C-4 raffinate streams, such as raffinate-1, and B—B streams from a butadiene plant. The accompanying examples illustrate the use of a typical raffinate-1.

The clays used as the basis of the catalyst to effect this reaction are montmorillonite silica-alumina clays. Chemically clays are composed primarily of silicon, aluminum and oxygen, with minor amounts of magnesium and iron in some cases. Variations in the ratios of these constituents, and their crystal lattice configurations, result in some fifty separate clays, each with its own characteristic properties. A group of catalysts which work well in this two-step method are acidic clay mineral catalysts.

The preferred group of clays is smectite clays. These clays have small particle size and unusual intercalation properties which afford them high surface area. They are alumina silicates having a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. This layering is illustrated in an article by F. Figueras, Catal. Rev.-Sci. Eng., 30, 457 (1988). What renders the smectites of particular interest among the clay minerals is their combination of cation exchange, intercalation and swelling properties.

The three-layer sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure which is particularly useful is:

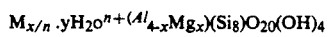

$$M_{x/n} \cdot yH_2O^{n+} (Al_{4-x}Mg_x)(Si_8)O_{20}(OH)_4$$

Where M represents the interlamellar (balancing) cation, normally sodium or lithium and x, y and n are integers.

Acidic montmorillonite clays are the preferred form of smectite clay in the present invention. Acids, including mineral acids such as sulfuric acid and phosphoric acid, activate montmorillonites by attacking and solubilizing structural cations in the octahedral layers. This opens up the clay structure and increases surface area. Preferably these acid clays should have acidities in the range of 0.1 to 30, or greater, mg KOH/gm, titrated to a phenolphthalein end point. Their surface area should be $>30$ m$^2$/g, and preferably 100 to 1000 m$^2$/g. Their moisture content should also be limited, which can be accomplished by heating to about 220° F., by which method the weight loss is generally less than 20 wt %.

Illustrative examples of suitable montomorillonite clays include Engelhard's Filtrol Grade 113 powder, having a residual acidity of 10 mg KOH/gm, a surface area of 300 m$^2$/g and a moisture content of 4 wt %; Filtrol Grade 13 powder, having an acidity of 15 mg KOH/g, a surface area of 300 m$^2$/g and a moisture content of 16 wt %; Filtrol Grade 24 granules of particle size 20/60 mesh, having an acidity of 16 mg KOH/g, a surface area of 300 m$^2$/g and a moisture content of 10 wt %; granular Filtrol Grade 224, of particle size 20/60, having an acidity of 3.0 mg KOH/g, a surface area of 350 m$^2$/g and a moisture content of $<1$ wt %; as well as extruded Filtrol Grade 62 which may be in 1/16" or 3/16" diameter extrudates and have an acidity of ca. 3.0 mg KOH/g.

Most preferred are montmorillonite clays with a residual titratable acidity in the range of 1 to 20 mg KOH/g, a surface area of 200 to 500 m$^2$/g and a moisture content of $<1\%$. Illustrative of such clays is Engelhard's Filtrol Grade 224 granules.

The two-step separation of isobutylene from a C-4 rich hydrocarbon stream can be conducted batchwise, or in a continuous slurry bed reactor, or in a fixed bed, continuous flow reactor. For practical reasons a fixed bed process is preferred for both steps.

The principal glycol ether products produced in Step 1 of this process will depend primarily upon the choice of glycol coreactant. In the case of ethylene glycol, the addition of the C-4 hydrocarbon feedstock rich in isobutylene results in the formation of ethylene glycol mono-t-butyl ether (EGTBE). When the substrate is 1,2-propylene glycol, the addition of isobutylene results in the formation of 1-t-butoxy-2-propanol (PGTBE-2OH) plus lesser amounts of 2-t-butoxy-1-propanol (PGTBE-1OH). Generally, the majority monoalkyl glycol ether products are formed in accordance with the Markovnikov rules of addition to the double bond of the isobutylene substrate and involve the primary (rather than the secondary) hydroxyl group of the glycol substrate. Small quantities of 1,2-dibutoxypropane (PGDTBE) may be formed during the deetherification of PGTBE.

The first step in separation of isobutylene is preferably accomplished at a generally lower temperature than the second step. Etherification is generally conducted at temperatures of from about 60° to 60° C. The preferred range is 100° C. to 140° C. The deetherification can be accomplished at a temperature of from about 100° to 220° C. The preferred temperature is from 160° to 200° C. The pressure can vary from 0 to 1000 psig. The preferred pressure for the deetherification step is as low as possible, e.g. from 0 to 300 psig. Optimum conditions may vary.

The resultant reaction mixture from the first step in the process (Eq. 1), the etherification reaction to give glycol mono-t-butyl ether, may comprise a single or bi-phase liquid product from which said glycol mono-t-butyl ether fractions may be recovered by the usual methods, including fractional distillation and liquid-liquid extraction, or via membrane technology. The resulting glycol mono-t-butyl ether, in crude or purified form is then, after possible dilution with additional glycol, fed in a second step (Eq. 2) to a deetherification reactor system also containing acidic montmorillonite clay catalyst. The regenerated isobutylene present in the effluent from the deetherification step may be easily recovered from unreacted glycol mono-t-butyl ether and glycol diluent by a simple stripping operation.

Typically the glycol mono-t-butyl ether intermediate is generated in up to about 5-10% concentration in the glycol-rich phase of the product effluent in the first, etherification step (Eq. 1). After recovery and dilution of said glycol mono-t-butyl ether in glycol diluent, the isobutylene is liberated in the second deetherification unit, also in up to 5-10% concentration.

These glycol ether and isobutylene concentrations are normally achieved in continuous processing at total liquid hourly space velocities (LHSV) of 1 to 5 under mild conditions.

Here LHSVs is defined as follows:

$$LHSV = \frac{\text{Volume of Total Liquid Feed Run Through The Reactor Per Hour}}{\text{Volume of Catalyst in Reactor}}$$

Typically conversion of the isobutylene fraction in the C-4 hydrocarbon stream to glycol mono-t-butyl ether during the etherification step is 10-90% per pass, using continuous unit equipment; conversion of said glycol mono-t-butyl ether, diluted with glycol, to isobutylene during deetherification is also typically 10-90%.

The accompanying Examples illustrate:
1) The etherification of the isobutylene fraction of a typical raffinate-1-stream to propylene glycol t-butyl ethers by reaction with a 1,2-propylene glycol over an acidic montmorillonite clay catalyst (Examples 1 and 3, Eq. 1). Here the highest isobutylene conversion is achieved at 120° C., using a LHSV of 1-2; the total propylene glycol t-butyl ether concentration (PGTBE-2-OH+1-OH) in the PG-rich phase of the effluent product is 3+ %, the 2-OH/1-OH isomer distribution is ca. 5:1. Estimated isobutylene conversion is 30%.
2) Deetherification of the propylene glycol t-butyl ether product from Example 1 to give pure isobutylene plus propylene glycol is illustrated in Example 2. Here the glycol ether feed is diluted with 1,2-propylene glycol and the catalyst is again acidic montmorillonite clay. Operating at 180° C., the propylene glycol t-butyl conversion per pass is ca. 70% (Eq. 2). Higher temperatures lead to break down of the propylene glycol and propylene glycol t-butyl ether to give a variety of unwanted by products.

3) The etherification of the isobutylene fraction of typical raffinate-1 to ethylene glycol t-butyl ether by selective reaction with ethylene glycol over acidic montmorillonite clay catalysts is illustrated in Example 4, followed by deetherification of the product phase at a higher temperature, using the same catalysts, in order to regenerate the isobutylene fraction (Example 5).

The examples which follow illustrate the two-step separation of isobutylene from a raffinate-1 feedstock using an acidic montmorillonite catalyst. The examples are only intended as a means of illustration and it should be understood that the invention is not meant to be limited thereby.

EXAMPLE 1

To a 50 cc capacity, plug flow, continuous reactor fitted with temperature and pressure controls, was charged 40 cc of Englehard Grade 224 clay, in granular form. A mixture of raffinate-1, containing ca. 12.7% isobutylene, plus 1,2-propylene glycol, were then fed separately to the reactor at rates of 16 cc/hr and 32 cc/hr respectively. The reactor was heated to temperature and a back pressure of 300 psi was maintained. After allowing the system to reach equilibrium by operating 4-6 hours, the effluent samples were collected in 316 ss pressure bombs. Each effluent sample comprised two layers, these were separated and analyzed.

The procedure was repeated at four different operating temperatures (60°-120° C). Analyses of the on-line product mixtures are summarized in Table I.

TABLE I

| | | | | | PROPYLENE GLYCOL t-BUTYL ETHER PRODUCTION | | | | | | | | | |
|---|---|---|---|---|---|---|---|---|---|---|---|---|---|---|
| | | | | | PRODUCT COMPOSITION (%) | | | | | | | | | |
| | | | | | Top Layer | | | | | | | Bottom Layer | | |
| | | Temp. | Flow | Sample | C-4 | | | C-4' | | | | PGTBE | | |
| Ex. | Catalyst | (°C.) | (cc/hr) | # | ISO | n | T-2 | 1- | ISO | C-2 | C-4's | 2-OH | 1-OH | PG |
| 1 | Clay-224 | | | FS | 10.8 | 31.6 | 17.5 | 12.2 | 12.7 | 13.4 | | | | |
| | | 60 | 16/32 | 1 | 11.1 | 32.6 | 17.2 | 12.0 | 12.3 | 13.1 | 6.8 | 0.1 | 0.1 | 92.8 |
| | | | | 2 | 11.1 | 32.6 | 17.2 | 12.0 | 12.3 | 13.1 | 7.8 | 0.1 | 0.1 | 91.8 |
| | | 80 | | 3 | 11.1 | 32.8 | 17.4 | 12.0 | 11.8 | 13.2 | 7.6 | 0.4 | 0.2 | 91.6 |
| | | | | 4 | 10.8 | 32.6 | 17.3 | 12.2 | 11.9 | 13.4 | 6.1 | 0.5 | 0.2 | 92.9 |
| | | 100 | | 5 | 11.3 | 33.2 | 17.5 | 12.2 | 10.7 | 13.3 | 5.9 | 1.3 | 0.4 | 92.3 |
| | | | | 6 | 11.2 | 33.2 | 17.5 | 12.2 | 10.7 | 13.3 | 7.2 | 1.2 | 0.4 | 91.0 |
| | | 120 | | 7 | 11.4 | 34.0 | 17.8 | 12.4 | 9.0 | 13.6 | 7.7 | 2.6 | 0.5 | 88.9 |
| | | | | 8 | 11.3 | 33.9 | 17.7 | 12.5 | 8.9 | 13.7 | 7.3 | 2.6 | 0.5 | 89.4 |

EXAMPLE 2

To a 50 cc capacity, plug flow, continuous reactor fitted with temperature and pressure controls, was charged 40 cc of Englehard Grade 224 clay, in granular form. Propylene glycol t-butyl ether, prepared by the method of Example 1, and diluted with 1,2-propylene glycol, was then fed to said reactor at a rate of 40 cc/hr. The reactor was heated to temperature and a back pressure of 100 psi was maintained. After allowing the system to reach equilibrium overnight, two effluent samples were collected in 316 ss pressure bombs and analyzed.

This procedure was repeated for six different operating temperatures (100°-220° C.). Analyses of the on-line product mixtures are summarized in Table II. Isobutylene product identification was by glc and gc/ms techniques.

TABLE II

| | | | | | PG t-Bu ETHER TO PC + C-4H$_8$ | | | | | |
|---|---|---|---|---|---|---|---|---|---|---|
| | | | Flow | | PRODUCT COMPOSITION (%) | | | | | |
| | | Temp. | Rate | Sample | ISO- | PGTBE | | PG | | |
| Ex. | Catalyst | (°C.) | (cc/hr) | # | C-4H$_8$ | 2-OH | 1-OH | DTBE | PG | Unknowns |
| 2 | Clay-224 | | | FS = 1 | | 9.4 | | | 90.5 | |
| | | 100 | 40 | 1 | 0.8 | 7.6 | 0.7 | | 89.5 | |
| | | | | 2 | 0.7 | 7.6 | 0.6 | | 90.0 | |
| | | 120 | | 3 | 1.7 | 6.6 | 0.8 | 0.1 | 90.3 | |
| | | | | 4 | 1.6 | 6.6 | 0.8 | 0.1 | 90.6 | |
| | | 150 | | 5 | 2.9 | 5.0 | 0.7 | 0.1 | 89.8 | |
| | | | | 6 | 2.6 | 5.0 | 0.7 | 0.1 | 90.6 | |
| | | 180 | | 7 | 4.6 | 2.3 | 0.4 | 0.1 | 85.0 | 2.3 2.0 |
| | | | | 8 | 4.7 | 2.7 | 0.4 | 0.1 | 85.9 | 1.8 1.6 |
| | | 180 | | 9 | 4.2 | 2.5 | 0.4 | | 88.4 | 1.3 1.3 |
| | | | | 10 | 3.8 | 2.3 | 0.4 | | 89.9 | 1.2 1.0 |
| | | 200 | | 11 | 6.0 | 0.9 | 0.2 | 0.2 | 79.7 | 4.3 3.9 |
| | | | | 12 | 6.4 | 0.7 | 0.2 | 0.2 | 78.5 | 4.2 4.2 |
| | | 220 | | 13 | 5.5 | 0.2 | 0.1 | 0.4 | 55.4 | 11.6 10.4 |
| | | | | 14 | 5.8 | 0.1 | 0.1 | 0.4 | 56.8 | 11.1 10.1 |

EXAMPLE 3

The experiment of Example 1 was repeated using the same Englehard Grade 224 catalyst, but the reactor system was this time fitted with a premixer for the Raffinate-1 and 1,2-propylene glycol feed streams. Six operating temperatures (60°-60° C.) were tested. The results are summarized in Table III.

TABLE III

PROPYLENE GLYCOL t-BUTYL ETHER PRODUCTION

| | | | | | PRODUCT COMPOSITION (%) | | | | | | | | |
|---|---|---|---|---|---|---|---|---|---|---|---|---|---|
| | | | | | Top Layer | | | | | | Bottom Layer | | |
| | | Temp. | Flow | Sample | C-4 | | C-4' | | | | | PGTBE | | |
| Ex. | Catalyst | (°C.) | (cc/hr) | # | ISO | n | T-2 | 1- | ISO | C-2 | C-4's | 2-OH | 1-OH | PG |
| 3 | Clay-224 | | | FS | 10.8 | 31.6 | 17.5 | 12.2 | 12.7 | 13.4 | | | | |
| | | 60 | 16/32 | 1 | 10.8 | 32.4 | 17.2 | 12.2 | 12.3 | 13.4 | 6.9 | 0.2 | 0.1 | 92.5 |
| | | | | 2 | 11.1 | 32.6 | 17.3 | 12.0 | 12.2 | 13.2 | 7.4 | 0.2 | 0.1 | 92.2 |
| | | 80 | | 3 | 11.0 | 32.8 | 17.3 | 12.2 | 11.5 | 13.3 | 6.8 | 0.7 | 0.3 | 92.2 |
| | | | | 4 | 10.8 | 32.9 | 17.3 | 12.2 | 11.7 | 13.3 | 6.1 | 0.5 | 0.2 | 93.1 |
| | | 100 | | 5 | 11.5 | 33.7 | 17.5 | 12.3 | 9.9 | 13.4 | 6.0 | 2.0 | 0.4 | 90.6 |
| | | | | 6 | 11.2 | 33.2 | 17.6 | 12.2 | 10.6 | 13.4 | 5.6 | 1.4 | 0.4 | 92.5 |
| | | 120 | | 7 | 11.3 | 33.7 | 17.8 | 12.4 | 9.5 | 13.6 | 6.1 | 2.5 | 0.4 | 90.7 |
| | | | | 8 | 11.3 | 33.6 | 17.8 | 12.3 | 9.7 | 13.5 | 5.8 | 2.3 | 0.4 | 91.4 |
| | | 140 | | 9 | 11.3 | 33.4 | 17.6 | 12.3 | 10.1 | 13.6 | 6.1 | 2.1 | 0.3 | 91.0 |
| | | | | 10 | 11.3 | 33.3 | 17.7 | 12.2 | 10.4 | 13.4 | 6.4 | 1.9 | 0.3 | 89.2 |
| | | 160 | | 11 | 11.0 | 33.0 | 17.6 | 12.1 | 11.1 | 13.5 | 4.4 | 1.1 | 0.2 | 92.8 |
| | | | | 12 | 11.1 | 33.0 | 17.6 | 12.1 | 11.1 | 13.4 | 5.0 | 1.1 | 0.2 | 92.2 |

EXAMPLE 4

Following the procedures of Example 1, the 50 cc capacity, plug flow, continuous reactor was charged with 40 cc of Englehard Grade 224 clay, in granular form, and a mixture of Raffinate-1, containing ca. 12.7% isobutylene and ethylene glycol were fed separately to the reactor at rates of 16 cc/hr and 32 cc/hr respectively. The reactor was heated to temperature and a back pressure of 300 psi was maintained. After allowing the system to reach equilibrium, the effluent samples were collected, and each sample separated into two layers and was analyzed.

The procedure was repeated at four different operating temperatures (80°–40° C.). Analyses of the on-line product mixtures are summarized in Table IV. Product compositions were confirmed by glc and gc/ir techniques.

TABLE IV

PROPYLENE GLYCOL t-BUTYL ETHER PRODUCTION

| | | | | | PRODUCT COMPOSITION (%) | | | | | | | | |
|---|---|---|---|---|---|---|---|---|---|---|---|---|---|
| | | | | | Top Layer | | | | | | | | |
| | | | | | C-4 | | | | | | | Bottom Layer | |
| | | Temp. | Flow | Sample | ISO | | C-4' | | | | | PGTBE | |
| Ex. | Catalyst | (°C.) | (cc/hr) | # | EG | n | T-2 | 1- | ISO | C-2 | C-4's | EGTBE | |
| 4 | Clay-224 | | | FS | 10.8 | 31.6 | 17.5 | 12.2 | 12.7 | 13.4 | | | |
| | | 80 | 16/32 | 1 | 10.7 | 32.2 | 17.5 | 12.1 | 12.3 | 13.5 | 1.5 | 0.1 | 93.3 |
| | | | | 2 | 10.8 | 32.2 | 17.5 | 12.1 | 12.3 | 13.4 | 1.5 | 0.1 | 96.0 |
| | | 100 | 16/32 | 3 | 10.8 | 32.4 | 17.4 | 12.1 | 12.1 | 13.5 | 0.8 | 0.4 | 97.1 |
| | | | | 4 | 10.9 | 32.3 | 17.5 | 12.1 | 12.1 | 13.4 | 1.4 | 0.3 | 98.0 |
| | | 120 | 16/32 | 5 | 10.7 | 32.5 | 17.7 | 12.1 | 11.6 | 13.7 | 1.3 | 0.7 | 97.6 |
| | | | | 6 | 10.9 | 32.4 | 17.5 | 12.2 | 11.7 | 13.4 | 1.3 | 0.7 | 97.6 |
| | | 140 | 16/32 | 7 | 11.0 | 32.5 | 17.5 | 12.2 | 11.6 | 13.4 | 1.7 | 0.8 | 96.9 |
| | | | | 8 | 10.9 | 32.5 | 17.6 | 12.2 | 11.4 | 13.5 | 1.3 | 0.9 | 97.3 |
| | | 120 | 9[a] | | | | | | | | 1.1 | 0.7 | 98.1 |

[a]Composite product from 3-day run

EXAMPLE 5

To the reactor system of Example 2 containing 40 cc of Engelhard Grade 224 granules, was charged the ethylene glycol, glycol monoalkyl ether rich product phase from Example 4, at a rate of 40 cc/hr. The reactor was heated to temperature and a back pressure of 100 psi was maintained. After allowing the system to reach equilibrium over 4–6 hours, two effluent samples were collected in 316 ss pressure bombs and analyzed.

The procedure was repeated for two different operating temperatures (180°–200° C.). Analyses of the on-line product mixture are summarized in Table V.

TABLE V

ETHYLENE GLYCOL t-BUTYL TO EG + C-4H$_8$

| | | | Flow | Sam- | Product Composition | | |
|---|---|---|---|---|---|---|---|
| | | Temp. | Rate | ple | ISO- | | |
| Ex. | Catalyst | (°C.) | (cc/hr) | # | C-4H$_8$ | EGTBE | PG |
| 5 | Clay-224 | | | FS | | 1.0 | 98.8 |
| | | 180 | 40 | 1 | 0.4 | 0.7 | 97.3 |
| | | | | 2 | 0.5 | 0.7 | 98.0 |
| | | 200 | 40 | 3 | 0.3 | 0.5 | 98.1 |
| | | | | 4 | 0.6 | 0.5 | 98.0 |

What is claimed is:

1. A two-step method for separating isobutylene from a C-4 hydrocarbon fraction comprising:

a) Contacting the C-4 fraction containing isobutylene with a glycol in the presence of an acidic montmorillonite catalyst at a temperature of about 60° to 160° C., thereby reacting the isobutylene with the glycol to yield a glycol mono-t-butyl ether, and subsequently b) reacting the glycol mono-t-butyl ether over the acidic montmorillonite catalyst at a temperature between 100° to 220° C. to produce the separated isobutylene.

2. The method of claim 1 wherein the glycol is selected from the group consisting of ethylene glycol and 1,2-propylene glycol.

3. The method of claim 1 wherein the montmorillonite catalyst is represented by the structure:

$$M_{x/n} \cdot yH_2O^{n+}(Al_{4-x}Mg_x)(Si_8)O_{20}(OH)_4$$

where M represents the interlamellar (balancing) cation, normally sodium or lithium and x, y and n are integers.

4. The method of claim 1 wherein the molar ratio of glycol to isobutylene fraction in the C-4 feed during formation of the desired glycol t-butyl ether is in the range of 10:1 to 100:1.

5. The method of claim 1 wherein the temperature range in the first step is from about 100° to 140° C.

6. The method of claim 1 wherein the temperature range in the second step is from about 160° to 200° C.

7. The process of claim 6 wherein the acidic montomorillonite clay has been activated by treatment with acid.

8. The process of claim 7 where the acid treated montmorillonite clay has a surface area in the range of 100 to 1000 m²/g.

9. The process of claim 7 wherein the acid montmorillonite clay has an acidity in the range of 0.1 to 30, or greater, mg KOH/gm, titrated to a phenolphthalein end point.

10. The process of claim 1 wherein the operating pressure is in the range of from zero to 1000 psig.

* * * * *